United States Patent
Yu et al.

(10) Patent No.: US 12,109,046 B2
(45) Date of Patent: Oct. 8, 2024

(54) DEVICES AND METHODS FOR DETERMINING A LEVEL OF FFI IN A LENS TISSUE

(71) Applicant: YuScan USA, LLC, Norcross, GA (US)

(72) Inventors: Nai-Teng Yu, Marietta, GA (US); Rong-Chun Yu, Diamond Bar, CA (US)

(*) Notice: Subject to any disclaimer, the term of this patent is extended or adjusted under 35 U.S.C. 154(b) by 799 days.

(21) Appl. No.: 17/336,419

(22) Filed: Jun. 2, 2021

(65) Prior Publication Data
US 2021/0372930 A1    Dec. 2, 2021

Related U.S. Application Data

(60) Provisional application No. 63/033,552, filed on Jun. 2, 2020.

(51) Int. Cl.
| | |
|---|---|
| *A61B 5/00* | (2006.01) |
| *A61B 3/117* | (2006.01) |
| *A61B 3/18* | (2006.01) |
| *G01J 1/60* | (2006.01) |

(Continued)

(52) U.S. Cl.
CPC .......... *A61B 5/6821* (2013.01); *A61B 3/1173* (2013.01); *A61B 3/18* (2013.01); *G01J 1/60* (2013.01); *G01N 2021/6471* (2013.01); *G06T 7/00* (2013.01)

(58) Field of Classification Search
CPC ....... A61B 5/6821; A61B 3/1173; A61B 3/18; G01J 1/60; G01N 2021/6471; G01N 21/6456; G01N 21/6486; G06T 7/00
See application file for complete search history.

(56) References Cited

U.S. PATENT DOCUMENTS

2010/0208207 A1*  8/2010  Connell, II ......... G06V 40/193
                                                351/210
2012/0203086 A1*  8/2012  Rorabaugh .......... A61B 5/0068
                                                600/321

(Continued)

OTHER PUBLICATIONS

Lagarto et al, Real Time Multispectral Fluorescence liftime iimaging using Single Photon Avalanche Diode Arrays, 2020, www.nature.com/Scientific Reports, 10 pages (Year: 2020).*

*Primary Examiner* — Lewis G West
(74) *Attorney, Agent, or Firm* — Josef L. Hoffmann; The Small Patent Law Group LLC (57) ABSTRACT

A method is provided that includes discriminating an autofluorescence (AF) response of a lens tissue of an eye due to a current level of 2-(2-furoyl)-4(5)-furanyl-1H-imidazole (FFI) in the lens tissue by interrogating a lens tissue of an eye along a visual axis of the eye by activating an illuminator for a select time to produce interrogating irradiation having a peak wavelength of 425 nm to 460 nm, the illuminator comprising at least one light source and a focal lens positioned with respect to the light source. The method also includes obtaining at least one image of the autofluorescence response of the lens tissue from a detector, the detector including a digital camera unit, analyzing the at least one image to determine a total autofluorescence index of the lens tissue, and determining a current level of FFI in the lens tissue based, at least in part, on the total autofluorescence index.

20 Claims, 6 Drawing Sheets

(51) Int. Cl.
*G01N 21/64* (2006.01)
*G06T 7/00* (2017.01)

(56) References Cited

U.S. PATENT DOCUMENTS

| | | | |
|---|---|---|---|
| 2014/0176905 A1* | 6/2014 | Nakano | A61B 3/102 |
| | | | 351/206 |
| 2021/0097683 A1* | 4/2021 | Yu | A61B 3/132 |
| 2024/0118208 A1* | 4/2024 | Prater | G01N 21/1717 |

* cited by examiner

DEVICES AND METHODS FOR DETERMINING A LEVEL OF FFI IN A LENS TISSUE

CROSS REFERENCE

This application claims the benefit of and priority to U.S. Provisional Patent Application Ser. No. 63/033,552, filed Jun. 2, 2020, entitled, "DEVICES AND METHOD FOR DETERMINING A LEVEL OF FFI IN A LENS TISSUE. The disclosure of this related applications is incorporated by reference in its entirety into this present application.

BACKGROUND

Embodiments herein generally relate to devices, methods, and systems for determining a level of 2-(2-furoyl)-4(5)-furanyl-1H-imidazole (FFI).

Early detection of a chronic or potentially chronic disease state of a patient can be of paramount importance in managing the long-term well-being of the patient. For example, diabetes mellitus is a chronic debilitating disease that impairs the ability of the body to metabolize sugar, resulting in inadequate control of glucose that, if left untreated, can lead to a variety of health complications. Once diagnosed, the diabetic must be under a treatment regimen for life.

Diabetes was the seventh leading cause of death in the United States in 2010 based on the 234,051 death certificates in which 69,071 diabetes was listed as the underlying cause of death. Diabetes may be under reported as a cause of death. Studies have found that only about 35% to 40% of people with diabetes who died had diabetes listed anywhere on the death certificate and about 10% to 15% had it listed as the underlying cause of death.

Before people develop type 2 diabetes, they almost always have "pre-diabetes"—average blood glucose levels that are higher than normal but not yet high enough to be diagnosed as diabetes. Doctors sometimes refer to pre-diabetes as impaired glucose tolerance (IGT) or impaired fasting glucose (IFG), depending on what test was used when it was detected. This condition indicates a higher risk for developing type 2 diabetes and cardiovascular disease. In some cases, it is possible to prevent or slow the development of type 2 diabetes in pre-diabetes patients with changes in diet and lifestyle.

Current methods for diabetes, IGT, and IGF screening, including utilizing random "finger stick" glucose (no fasting), are no longer recommended by healthcare authorities because the random nature of the test lacks sensitivity and specificity. Due to the pain of a finger stick or blood draw and the poor performance of these tests, many individuals avoid current diabetes screening programs. Also, in the U.S. the current rules (Clinical Laboratory Improvement Act of 88, CLIA 88) regulating blood testing in physicians' offices or alternate sites make this type of screening difficult to carry out. Glucose urine testing, the most common method of diabetes screening, has even lower test sensitivity and specificity. Due to the insufficiency of current methods for diabetes, IGT, and IGF screening, many diabetics go undetected for many years and many pre-diabetes patients progress to type 2 diabetes. In fact, a large percentage of diabetics who are detected using current methods in the United States (600,000 per year) have late-stage complications due to type 2 diabetes. Accordingly, it is desirable to provide convenient, painless, accurate, and non-invasive methods and systems for that enable detection of a chronic or potentially chronic disease state of a patient.

BRIEF DESCRIPTION

In one or more embodiments, a method is provided that includes, under control of one or more processors configured with executable instructions, discriminating an autofluorescence (AF) response of a lens tissue of an eye due to a current level of 2-(2-furoyl)-4(5)-furanyl-1H-imidazole (FFI) in the lens tissue. The AF response is discriminated by interrogating a lens tissue of an eye along a visual axis of the eye by activating an illuminator for a select time to produce interrogating irradiation having a peak wavelength of 425 nm to 460 nm, the illuminator comprising at least one light source and a focal lens positioned with respect to the light source. The AF response is also discriminated by obtaining at least one image of the autofluorescence response of the lens tissue from a detector, the detector including a digital camera unit, analyzing the at least one image to determine a total autofluorescence index of the lens tissue, and determining a current level of FFI in the lens tissue based, at least in part, on the total autofluorescence index.

Optionally, the at least one light source includes one or more of a laser diode or a light-emitting diode (LED). In one aspect, interrogating further comprises activating the illuminator to produce interrogating radiation having a peak wavelength of 434 nm. In another aspect, the method also includes obtaining the at least one image during or immediately subsequent to the select time. In one example, the select time is from 2 seconds to 30 seconds. In another example, the one or more processors are further configured to sequentially repeat the interrogating and obtaining to obtain 2 to 30 images. In one embodiment, transmitting the at least one image to a remote electronic device via a wireless connection over a network. In another embodiment, the at least one light source further comprises an array of at least three light sources and interrogating includes pulsing each of the at least three light sources on and off at unique intervals with respect to the remaining ones of the at least three sources.

Optionally, the at least one image comprises a plurality of candidate images, and the method also includes analyzing each candidate image of the plurality of candidate images to determine a symmetry value and a definition value of a pupil spot of a pupil, and determining at least one confirmed image from the plurality of candidate images based on the symmetry value and the definition value. The method can include discerning a median location of a peak value of the at least one confirmed image, and determining the total autofluorescence index based, at least in part, on calculating an average of an area of the median location of the peak value of the at least one confirmed image. In one aspect, the median location of the peak value comprises at least an N by N area of pixels. In another aspect, the at least and N by N area comprises at least a 5 pixel by 5 pixel area. In one example, determining the total autofluorescence index includes calculating a normalized total autofluorescence value based on a total autofluorescence value of the at least one confirmed image normalized by the area of the median location. In another example, determining the total autofluorescence index further comprises normalizing the normalized total autofluorescence value with a calibration value. In one embodiment, the calibration value comprises a total calibration autofluorescence index. In another embodiment, determining the total calibration autofluorescence index comprises determining a total calibration autofluorescence value based on at least one calibration image normalized by an area of a calibration median location to determine the total calibration autofluorescence value.

In one or more embodiments, a computer program product comprising a non-transitory computer readable storage medium comprising computer executable code to discriminate an autofluorescence (AF) response of a lens tissue of an eye due to a current level of 2-(2-furoyl)-4(5)-furanyl-1H-imidazole (FFI) in the lens tissue. The AF is discriminated by interrogating a lens tissue of an eye along a visual axis of the eye by activating an illuminator for a select time to produce interrogating irradiation having a peak wavelength of 425 nm to 460 nm, the illuminator comprising at least one light source and a focal lens positioned with respect to the light source. The AF is also discriminated by obtaining at least one image of the autofluorescence response of the lens tissue from a detector, the detector including a digital camera unit, analyzing the at least one image to determine a total autofluorescence index of the lens tissue, and determining a current level of FFI in the lens tissue based, at least in part, on the total autofluorescence index.

Optionally, the computer executable code to also, as part of the interrogating, activate the illuminator to produce interrogating radiation having a peak wavelength of 434 nm. In one aspect, the computer executable code to also, as part of the obtaining, obtaining the at least one image during or immediately subsequent to the select time. In another aspect, the select time is from 2 seconds to 30 seconds. In one example, the computer executable code to also, sequentially repeat the interrogating and obtaining to obtain 2 to 30 images. In another example, the computer executable code to also, transmit the at least one image to a remote electronic device via a wireless connection over a network.

Optionally, the at least one image includes a plurality of candidate images, and includes executable code to analyze each candidate image of the plurality of candidate images to determine a symmetry value and a definition value of a pupil spot of a pupil, determine at least one confirmed image from the plurality of candidate images based on the symmetry value and the definition value, discern a median location of a peak value of the at least one confirmed image, and determine the total autofluorescence index based, at least in part, on calculating an average of an area of the median location of the peak value of the at least one confirmed image. In one aspect, the median location of the peak value comprises at least an N by N area of pixels. In another aspect, the at least and N by N area comprises at least a 5 pixel by 5 pixel area. In one example, the computer executable code to also, as part of determining the total autofluorescence index, calculate a normalized total autofluorescence value based on a total autofluorescence value of the at least one confirmed image normalized by the area of the median location. In another example, the computer executable code to also, as part of determining the total autofluorescence index, normalize the normalized total autofluorescence value with a calibration value. In one embodiment, the calibration value includes a total calibration autofluorescence index. In another embodiment, the computer executable code to also, determine a total calibration autofluorescence value based on at least one calibration image normalized by an area of a calibration median location.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

U.S. Pat. No. 5,203,328 to Samuels entitled, "Apparatus and Methods for Quantitatively Measuring Molecular Changes in the Ocular Lens" is hereby incorporated by reference in its entirety. "Development of a noninvasive diabetes screening device using the ratio of fluorescence to Rayleigh scattered light" by Yu et al. (Journal of Biomedical Optics 1(3), 280-288 (July 1996)) is also hereby incorporated by reference in its entirety.

As used herein, "determining a disease state" shall mean determining one or more of (i) a presence or likelihood a disease state, (ii) a degree of progression of a disease state, (iii) a change in the presence, likelihood, or progression of a disease state, (iv) a probability of having, not having, developing, or not developing a disease state, or (v) the presence, absence, or likelihood of complications from a disease state. For example, determining a disease state may include one or more of (i) determining the presence or likelihood of diabetes mellitus and/or dementia (e.g., Alzheimer's disease); (ii) determining the degree of progression of diabetes mellitus and/or dementia; (iii) determining a change in the presence, likelihood, or progression of diabetes mellitus and/or dementia; (iv) determining a probability of having, not having, developing, or not developing diabetes mellitus and/or dementia; or (v) determining the presence, absence, progression, or likelihood of complications from diabetes mellitus and/or dementia.

The terms "diabetes" and "diabetes mellitus" shall mean a blood glucose regulation condition, including Type I, Type II, and gestational diabetes, other types of diabetes as recognized by the American Diabetes Association (See ADA Committee Report, Diabetes Care, 2003) and similar governing bodies, hyperglycemia, impaired fasting glucose (IFT), impaired glucose tolerance (IGT), and prediabetes.

The term "Alzheimer's disease" shall mean a progressive degenerative disease of the brain that leads to dementia. On a cellular level, Alzheimer's disease may be characterized by an extent of presence of neurofibrillary tangles in nerve cells of the brain. In the brain, Alzheimer's disease involves degeneration of the cortical regions, especially the frontal and temporal lobes. Type II diabetes causes brain insulin resistance, oxidative stress, and cognitive impairment; therefore, Alzheimer's disease may be considered as Type III diabetes. AD represents a form of diabetic complication in the brain that has molecular and biochemical features that overlap with both Type I and Type II diabetes mellitus.

The term "spectral response" shall mean any ocular tissue reflectance characteristic indicative of one or more of an autofluorescence response of a target tissue, a level of fluorescence intensity or a ratio of a level of fluorescence intensity to a level of scattered light, or any reflectance property of tissue that is useful for estimating the intrinsic fluorescence and Rayleigh scattering spectrum for a target tissue. In one non-limiting example, the spectral response can include one or more of the presence, intensity, change in intensity, or rate of change in intensity of autofluorescence of a target tissue at a select time and/or over a select period of time.

The terms "level of 2-(2-furoyl)-4(5)-furanyl-1H-imidazole (FFI)" and "level of FFI" shall mean any measure of the presence, time, extent, state, or rate of accumulation of FFI in a target tissue associated with a disease state, including, as examples, measurements of the presence, concentration, or change in concentration of FFI in tissue; measurements of the rate or change in the rate of the accumulation of FFI; measurements of the presence, intensity, or change in intensity of fluorescence and the Rayleigh back scatter alone or, in combination, known to be associated with FFI; and measurements of the rate or change in the rate of the accumulation of FFI.

The term "obtain" or "obtaining", as used in connection with data, signals, measurements, information and the like, includes at least one of i) accessing memory of a local external device or resource manager where the data, signals, information, etc. are stored, ii) receiving the data, signals, information, etc. over a wireless communications link between the client device and a local external device, and/or iii) receiving the data, signals, information, etc. at a resource manager over a network connection. The obtaining operation, when from the perspective of a client device, may include sensing new signals in real time, and/or accessing memory to read stored data, signals, information, etc. from memory within the client device. The obtaining operation, when from the perspective of a local external device, includes receiving the data, signals, information, etc. at a transceiver of the local external device where the data, signals, information, etc. are transmitted from a client device and/or a resource manager. The obtaining operation may be from the perspective of a resource manager, such as when receiving the data, signals, information, etc. at a network interface from a local external device and/or directly from a client device. The resource manager may also obtain the data, signals, information, etc. from local memory and/or from other memory, such as within a cloud storage environment and/or from the memory of a workstation.

When light is described as having a "single wavelength" or a "peak wavelength", it is understood that the light can actually comprise light at a plurality of wavelengths, but that a significant portion of the energy in the light is transmitted at a single wavelength or at a range of wavelengths near a single wavelength (e.g., 434 nm with a tolerance of +/−10 nm, 495 nm with a tolerance of +/−20 nm, and the like).

Figure 1:
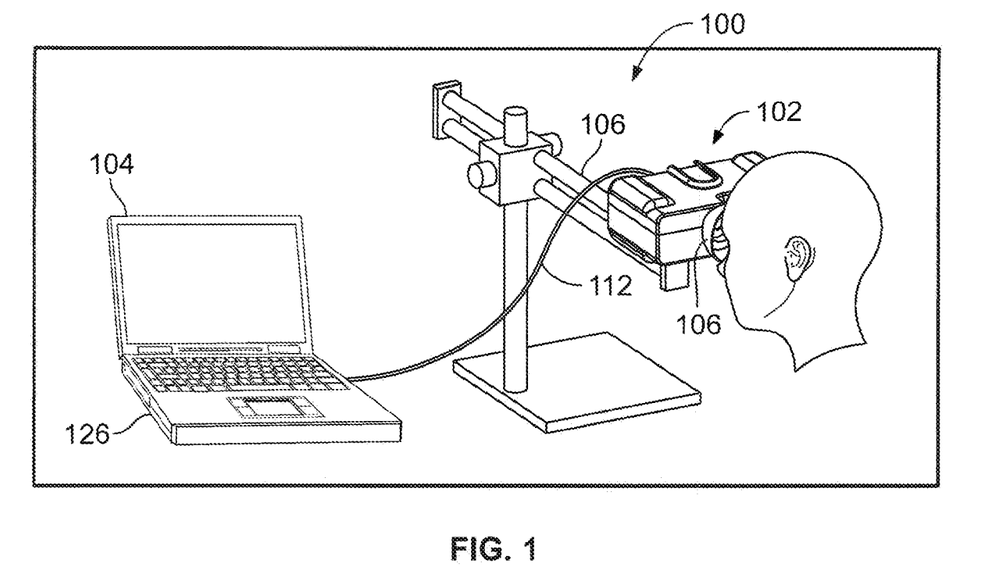
FIG. 1 illustrates an example system for determining a level of FFI in a lens tissue in accordance with embodiments herein.

FIG. 1 illustrates an example system for determining a level of FFI based on total lens fluorescence in accordance with embodiments herein. The system 100 includes a total lens fluorescence (TLF) unit 102 (e.g., a client device) for interrogating at least a lens tissue of an eye by activating an illuminator for a select time and obtaining at least one measurement of the autofluorescence response of the lens tissue at a detector during or immediately following the select time in accordance with embodiments herein. The system 100 includes an electronic device 104 (e.g., an external electronic device and/or a resource manager) operably coupled to the TLF unit 102 for sending instructions to the TLF unit 102, obtaining measurements of total lens fluorescence from the TLF unit 102, and determining a level of FFI based on measurements of total lens fluorescence in accordance with embodiments herein. In one example, the TLF unit 102 may be mounted on a stand 106 for stabilizing the TLF unit 102. Additionally or alternatively, the TLF unit 102 and the electronic device 104 may be integrated into a common housing.

Figure 2A:
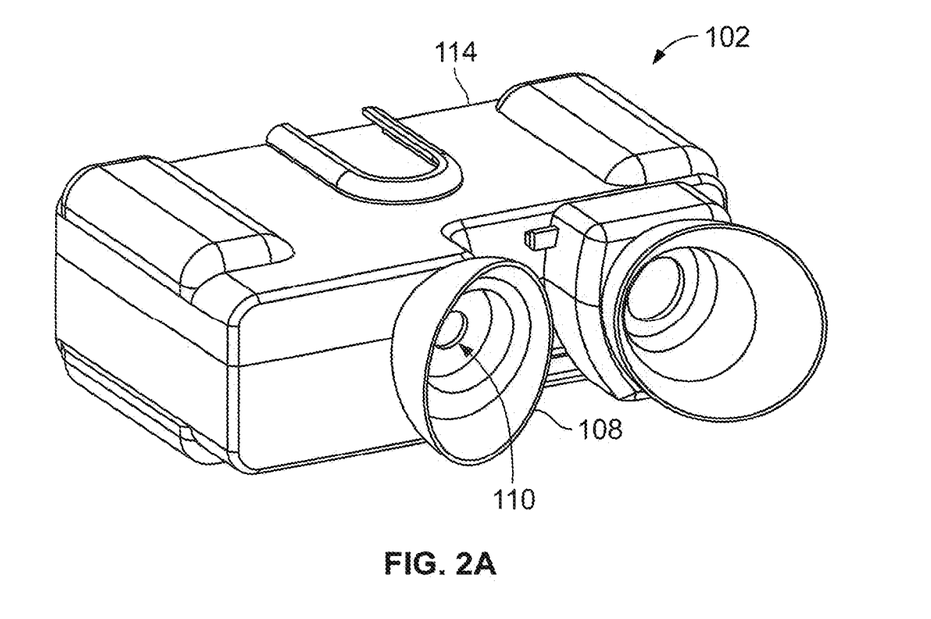
FIGS. 2A and 2B illustrate, respectively, a front perspective view and a rear perspective view of a device for determining a level of FFI in a lens tissue in accordance with embodiments herein.
Figure 2B:
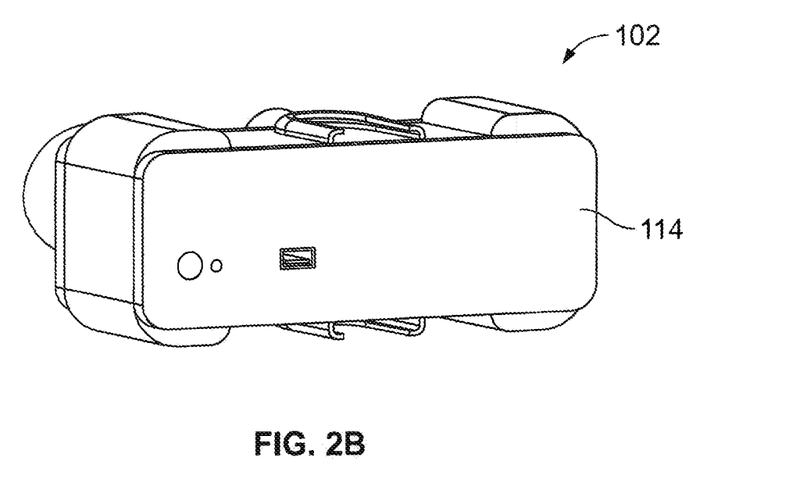

FIGS. 2A and 2B illustrate, respectively, a front perspective view and a rear perspective view of an example of a TLF unit 102 for determining a level of FFI based on total lens fluorescence in accordance with embodiments herein. The TLF unit 102 includes a housing 114 having an eye aperture 110 disposed therein through which measurements are obtained. In one example, the TLF unit 102 may include at least one eyecup 108 disposed on an exterior of the housing 114 of the TLF unit 102 about the eye aperture 110. The eye cup 108 receives the eye of the patient, positions the eye of the patient with respect to the aperture 110, and stabilizes the eye with respect to the illuminator and detector contained within the housing of the TLF unit 102. In an example, the electronic device 104 transmits instructions to and obtains data from the TLF unit 102 over a wired connection 112 (e.g., a USB cable, or the like). In an additional or alternative example, the electronic device 104 transmits instructions to and obtains data from the TLF unit 102 over a wireless connection (e.g., a network connection, Bluetooth connection, or the like).

Figure 3:
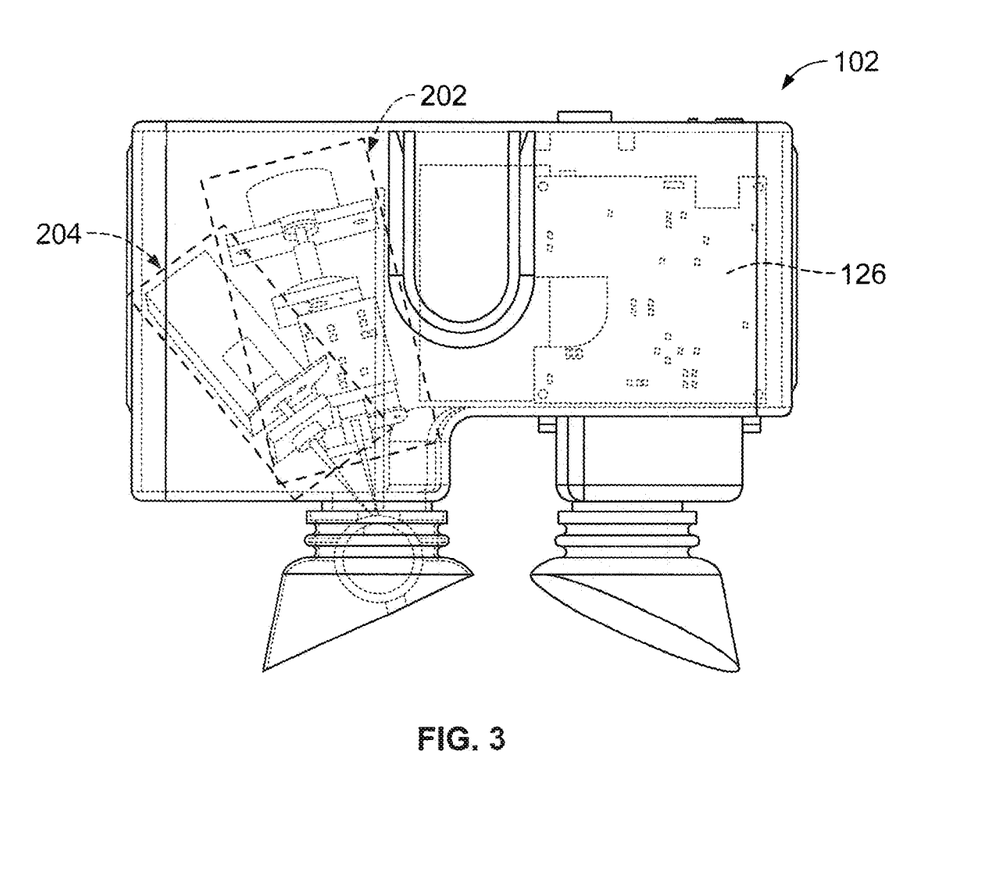
FIG. 3 illustrates example aspects of the device of FIGS. 2A and 2B in accordance with embodiments herein.
Figure 4:
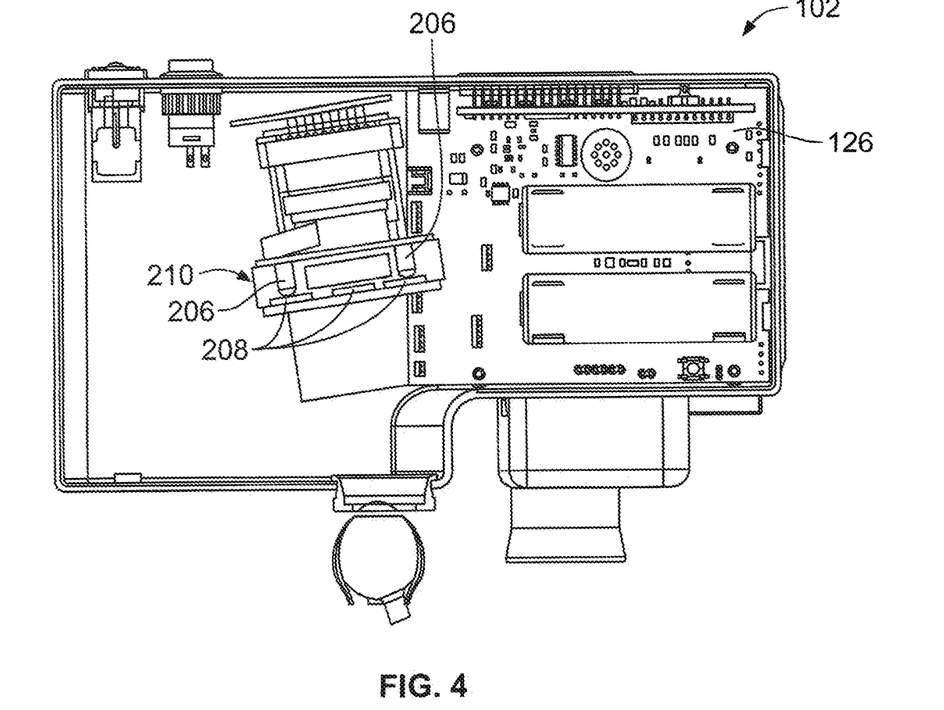
FIG. 4 illustrates example aspects of the device of FIGS. 2A and 2B in accordance with embodiments herein.

FIGS. 3 and 4 illustrate example aspects of the TLF unit 102 of FIGS. 2A and 2B. The TLF unit 102 interrogates at least a lens tissue of an eye by activating an illuminator 202 for a select time and obtaining at least one measurement of the autofluorescence response of the lens tissue at a detector 204 during or immediately following the select time in accordance with embodiments herein. The illuminator 202 includes at least one light source 206 (e.g., a light-emitting diode (LED), a laser, and the like) for generating excitation radiation for illuminating a target tissue L of an eye of a patient, at least one lens 208 positioned with respect to the at least one light source 206 to produce interrogating radiation. The at least one light source 206 may be fixed with respect to the eye aperture 110 disposed in the housing 114. The at least one light source 206 may have a peak wavelength of 425 nm to 460 nm (e.g., 434 nm). The at least one light source 206 may produce blue and/or violet light. The at least one light source 206 may include a laser diode or a light-emitting diode (LED). In one example, the light source 206 includes a Thorlabs 430L LED. In the example, the light source 206 may emit 8 mw of light from an approximately 100 micron diameter LED that may be at least partially collimated by a 3 mm ball lens into a 22 degree cone. The illuminator 202 may also include a narrow bandpass filter positioned between the at least one light source and the eye aperture 110. In one example, the light from the light source 206 is filtered by a filter 212. The filter 212 may be a high efficiency narrowband filter (e.g., a filter having a bandpass of 17-20 nm centered on 434 nm). The filter 212 may reduce the total output power of the light source 206 (e.g., from 8 mw to 4 mw). A surface of the filter 212 may be positioned a select distance (e.g., 6 cm) from a nominal eye position as measured from the cornea of the eye of a patient. The detector 204 includes a sensor 214. The sensor 214 may include a digital camera unit to image the fluorescence response of the eye during or immediately after exposure to interrogating radiation from the light source 206. The digital camera unit 214 may be a 5 MP camera. The detector 204 may also include a detector filter 216 positioned between the sensor 214 and the eye aperture 110. In one example, the filter 216 may be centered on 495 nm with a bandpass of 17-20 nm.

Figure 5:
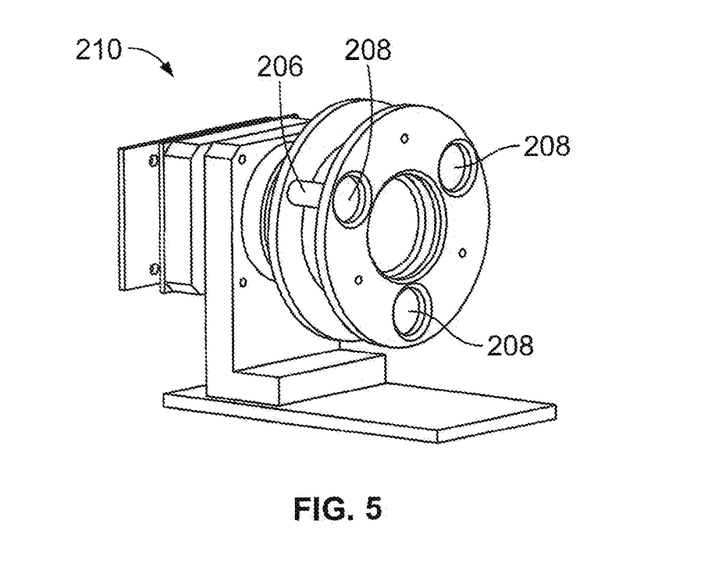
FIG. 5 illustrates an example of an illumination wheel in accordance with embodiments herein.
Figure 6:
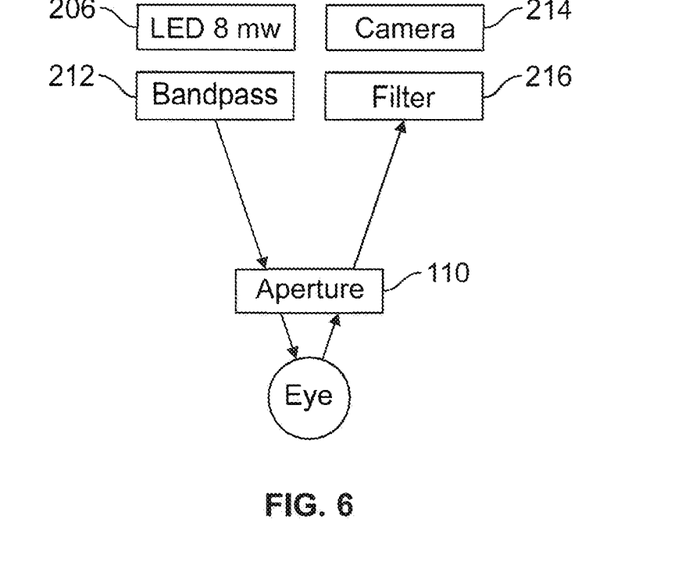
FIG. 6 illustrates one example of an optical arrangement in accordance with embodiments herein.

Optionally, the light source 206 may include an illumination wheel 210 (shown in at least FIGS. 4 and 5) and the at least one light source 206 may include an array of light sources 206 (e.g., three light sources) that are spaced about a central point of an illumination wheel 210. The array of light sources 206 may be radially equally spaced about the central point. Each of the at least three light sources 206 may be configured to interrogate a unique retinal location. Each of the at least three light sources 206 may be pulsed on and off at unique intervals with respect to the remaining ones of the at least three light sources 206.

Division and processing of responding radiation received by the detector 204 may occur in the detection and processing assembly (DPA) 126. The DPA 126 may be implemented on, or partially on, one or both of the TLF unit 102 and the external electronic device 104.

The DPA 126 may include components such as one or more processors 152 (e.g., a microprocessor, microcomputer, application-specific integrated circuit, etc.), one or more local storage medium (also referred to as a memory) 154, a user interface 144 which includes one or more input circuits 145 and one or more output circuits 148, a power module 156, a component interface 158, and one or more wireless transceivers 162. All of these components can be operatively coupled to one another, and can be in communication with one another, by way of one or more internal communication links, such as an internal bus.

The input circuit 145 receives user instructions in various manners at the user interface 144. The processors 152 execute instructions stored in the memory 154 to interpret and perform actions based on user instructions that are received through the input circuit 145. The user instruction may be an instruction to perform one or more measurements of the target tissue or an instruction to perform various types of actions and/or execute various types of commands, as described herein.

Figure 7:
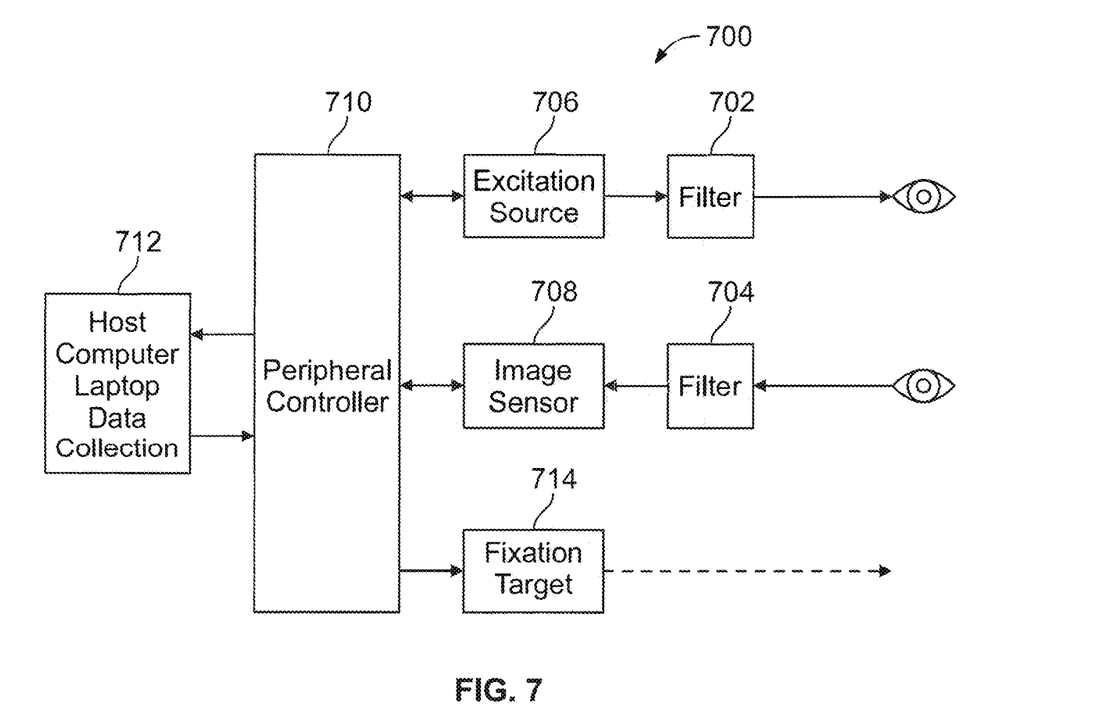
FIG. 7 illustrates aspects of operation of the system of FIG. 1 and a process for determining a level of FFI in a lens tissue in accordance with embodiments herein.

With further reference to FIG. 7, an emitted radiation analysis (ERA) application 160 implemented on the TLF unit 102 and/or the electronic device 104 receives user-generated instructions to perform one or more measurements on a target tissue and, based thereon, discriminates an autofluorescence response of a target tissue of an eye due to a current level of FFI in the target tissue. The ERA application 160 discriminates an autofluorescence response of a target tissue of an eye due to a current level of FFI in the target tissue by interrogating at least a lens tissue of an eye by activating the illuminator for a select time to produce interrogating radiation having a peak wavelength of 425 nm to 460 nm (e.g., 434 nm). The illuminator includes at least one light source and a focal lens positioned with respect to the light source to produce interrogating radiation directed along a visual axis of the eye. The at least one light source may be fixed relative to an eye aperture disposed in a housing of the device and the eye aperture may facilitate alignment of the interrogating irradiation with respect to the visual axis of the eye. The ERA application 160 obtains at least one image of the autofluorescence response of the lens tissue (e.g., as viewable through a pupil of the eye) from the detector. The detector is operable to image the autofluorescence response of the lens tissue. The detector includes, as a sensor, a digital camera unit (e.g., a two-dimensional CCD digital camera unit configured with pixels meeting or exceeding threshold levels of uniformity and linear response). Additionally or alternatively, a computer algorithm may be used to compensate for nonlinearity. Additionally or alternatively, the detector includes, as a sensor, a point detector avalanche photodiode (APD). The APD may be configured to have a high quantum efficiency in the 470-550 nm spectral region and a linear response. The ERA application 160 may activate the illuminator for a select time (e.g., 2 s to 30 s) per measurement and, during or immediately subsequent to the select time, activate the detector to obtain at least one image corresponding to the measurement. The ERA application 160 may sequentially perform the interrogating and obtaining to obtain 2 to 30 measurements. The ERA application 160 transmits the at least one image to a remote electronic device via one or more of a wired or a wireless connection. In one example, the ERA application 160 illuminates the target tissue L of the eye with excitation radiation having a peak wavelength of 425 nm to 460 nm (e.g., 434 nm) and measures the autofluorescence response of the target tissue due to the current level of FFI. In an example, the at least one light may include an array of at least three light sources and the ERA application 160 may interrogate the lens tissue by pulsing each of the at least three light sources on and off at unique intervals with respect to the remaining ones of the at least three sources. The ERA application 160 may transmit the at least one image to a remote electronic device via one or more of a wired or a wireless connection.

The DPA 126 includes an output circuit 148 and one or more wireless transceivers 162, one or both of which may output measurements of the target tissue and related data, and associated requests, to one or more remote electronic devices over a network 111. The DPA 126 may be configured to access the network 111 over a wired or wireless connection. As non-limiting examples, the DPA 126 may access the network 111 through a wireless communications channel and/or through a network connection (e.g., the Internet). Additionally or alternatively, the DPA 126 may include a wired or wireless communication terminal, such as a desktop computer, laptop computer, and the like.

The DPA 126 may be configured to access the network resources 118, including web-based or network-based data, applications, and services, via the network 111. The network 111 may represent one or more of a local area network (LAN), a wide area network (WAN), an Intranet or other private network that may not be accessible by the general public, or a global network, such as the Internet or other publicly accessible network. The network 111 provides communication between the DPA 126, one or more remote electronic device, and one or more network resources 118. It will be understood that, in some embodiments, the network resources 118 may represent a single entity or one or more physical or virtual servers that are configured to deliver online resources to the DPA 126. Examples of the network resources 118 include, but are not limited to, web-based or network-based data storage services, web-based or network-based patient management services, and the like.

The user interface 144 permits the user to operate the DPA 126 for any of its intended purposes, such as administering the ERA application 160, operating software applications, electronic communication, and the like. The input circuit 145 can include one or more of a visual input device, such as an optical sensor or camera, and/or a mechanical input circuit such as a keyboard, keypad, selection hard and/or soft buttons, switch, touchpad, touch screen, icons on a touch screen, a touch sensitive areas on a touch sensitive screen and/or any combination thereof that are configured to receive input (e.g., instructions, requests) from the user. The output 148 can include one or more electronic devices, such as a display 166, that are configured to communicate output measurements of the target tissue and related data and/or content to the user. For example, the output circuit 148 can include a visual output circuit such as a liquid crystal display screen, touch sensitive screen, a non-touch sensitive screen, a text-only display, a smart phone display, an audio output (e.g., a speaker or headphone jack), and/or any combination thereof and/or one or more light emitting diode indicators. The output circuit 148 is integral to (e.g., within a common housing) at least the DPA 126.

The memory 154 may encompass one or more memory devices of a variety of forms (e.g., read only memory, random access memory, static random-access memory, dynamic random-access memory, etc.) and can be used by the processor 152 to store and retrieve data. The data that is stored by the memory 154 can include, but need not be limited to, operating systems, applications, user collected content, and informational data. Each operating system includes executable code that controls basic functions of the device, such as interaction among the various components, communication with external devices via the wireless transceivers 162, the component interface 158, and storage and retrieval of applications and data to and from the memory 154. Each application includes executable code that utilizes an operating system to provide more specific functionality for the communication devices, such as file system service and handling of protected and unprotected data stored in the memory 154.

The memory 154 stores various content including, but not limited to, the ERA application 160. The ERA application 160 includes instructions accessible by the one or more processors 152 to direct the processor 152 to implement the methods, processes and operations described herein including, but not limited to, the methods, processes and operations illustrated in the Figures and described in connection with the Figures. In an alternative embodiment, the ERA application 160 may operate from one or more storage medium (also referred to as cloud storage).

Figure 8:
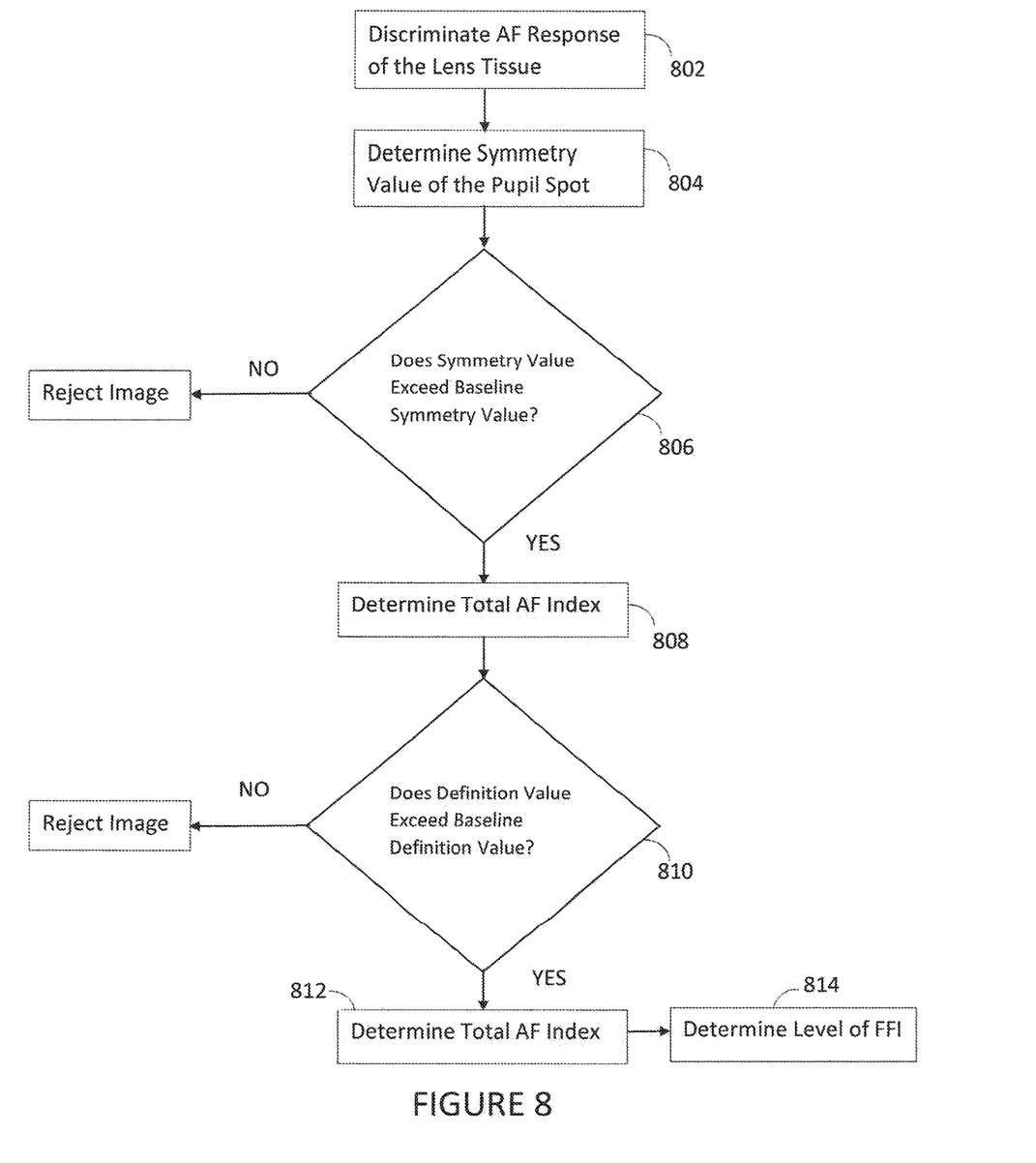
FIG. 8 illustrates an example process for determining a level of FFI in a lens tissue in accordance with embodiments herein.

FIG. 8 illustrates an example method 800 for determining a level of FFI based on discriminating an autofluorescence response of a target tissue due to FFI in accordance with embodiments herein. The method 800 may be performed utilizing the systems and methods described in detail in relation to FIGS. 1-7. A portion of the operations of FIG. 8 may be implemented by one or more processors of the optical system 100 configured with executable instructions. It should be recognized that while the operations of the method 800 are described in a somewhat serial manner, one or more of the operations of the method 800 may be continuous and/or performed in parallel with one another. For example, the various operations of the optical system 100 may be continuous and/or performed in parallel with one another and/or other functions of the optical system.

Beginning at 802, one or more processors discriminate an autofluorescence (AF) response of a lens tissue of an eye due a current level of FFI in the lens tissue. Discriminating the autofluorescence response due to the current level of FFI includes minimizing or eliminating any autofluorescence response due to the presence of any other AGE in the lens tissue. The discriminating operation includes interrogating a lens tissue of an eye along a visual axis of the eye by activating an illuminator for a select time to produce interrogating irradiation having a peak wavelength of 425 nm to 460 nm. For example, the one or more processors of the DPA direct the at least one light source 102 to illuminate a target tissue L of an eye with the excitation radiation having a peak wavelength of 434 nm. The select time may be from 2 seconds to 30 seconds. Additionally or alternatively, the at least one light source may include an array of at least three light sources and interrogating may include pulsing each of the at least three light sources on and off at unique intervals with respect to the remaining ones of the at least three sources.

The discrimination operation also includes obtaining at least one image of the autofluorescence response of the lens tissue from a detector. The detector may include a digital camera unit. Optionally, the one or more processors may sequentially repeat the interrogating and obtaining to obtain 2 to 30 candidate images. The AF response due to the current level of FFI may include one or more of an autofluorescence response, a level of fluorescence intensity or a ratio of a level of fluorescence intensity to a level of scattered light. The process may measure, as the AF response, one or more of the presence, intensity, change in intensity, or rate of change in intensity of autofluorescence of the target tissue L over a select time. Optionally, the process may measure an ensemble of AF responses and utilize a mathematical operation (e.g., averaging, mean, median, and the like) to combine the AF responses to form resultant AF response.

At 804, the one or more processors analyze each candidate image to determine a symmetry value of a pupil spot of a pupil. Analyzing may include discerning a median location of a peak value of the candidate image.

At 806, the one or more processors determine whether the symmetry value of each candidate image exceeds a baseline symmetry value. Based on the symmetry value of a candidate image falling below the baseline symmetry value, the candidate image is rejected. Based on the symmetry value of a candidate image exceeding the baseline symmetry value, flow moves to 808.

At 808, the one or more processors analyze each candidate image to determine a definition value of a pupil spot of a pupil.

At 810, the one or more processors determine whether the definition value of each candidate image exceeds a baseline definition value. Based on the symmetry value of a candidate image falling below the baseline definition value, the candidate image is rejected. Based on the definition value of a candidate image exceeding the baseline definition value, the candidate image is determined to be a confirmed image and flow moves to 812.

At 812, the one or more processors analyze the at least one image to determine a total autofluorescence index of the lens tissue. Determining the total autofluorescence index may include calculating an average of an area of the median location of the peak value of the at least one confirmed image. The median location of the peak value may include at least an N by N area (e.g., at least a 5×5 area) of pixels. Additionally or alternatively, determining the total autofluorescence index may include calculating a normalized total autofluorescence value based on a total autofluorescence value of the at least one confirmed image normalized by the area of the median location. Further additionally or alternatively, determining the total autofluorescence index may include normalizing the normalized total autofluorescence value with a calibration value. The calibration value may be a total calibration autofluorescence index. Determining the total calibration autofluorescence index may include determining a total calibration autofluorescence value based on at least one calibration image normalized by an area of a calibration median location to determine the total calibration autofluorescence value.

At 814, the one or more processors determine a current level of FFI in the lens tissue based, at least in part, on the total autofluorescence index. Optionally, at 814, one or more processors may determine, as the current level of FFI, the ratio of the FFI spectral response to the total AGE spectral response of the target tissue. Optionally, the process may, based on measuring an ensemble of FFI and/or total AGE total autofluorescence indices and utilizing a mathematical operation (e.g., averaging, mean, median, and the like) to combine the FFI and/or total AGE total autofluorescence indices to form a resultant total autofluorescence index, analyze the resultant total autofluorescence index to determine the current level of FFI in the target tissue L.

In one example, when the method is utilized, a 21 by 21 pixel area may be provided of a median location of a peak value of an image. In another example, the total lens fluorescence values for a left eye may be 101, 90, 98, 100, 90, 118, 100, and 101. As a result, a mean of 99.8 is provided with a standard deviation of 8.7 and a calibration value of 8.7 that is less than 15% and considered reliable. Meanwhile, the left eye can have three values, 68, 78, and 69 with a mean of 71.7, a standard deviation of 5.5, a calibration value of 7.7 being less than 15% and reliable.

Figure 9A:
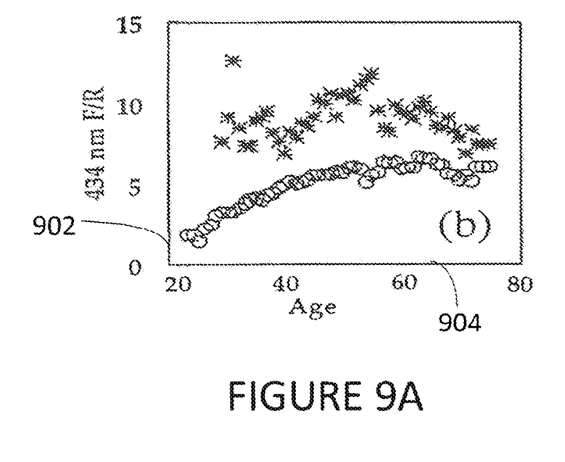
FIG. 9A illustrates a graph utilized for comparing current FFI values in accordance with embodiments herein.
Figure 9B:
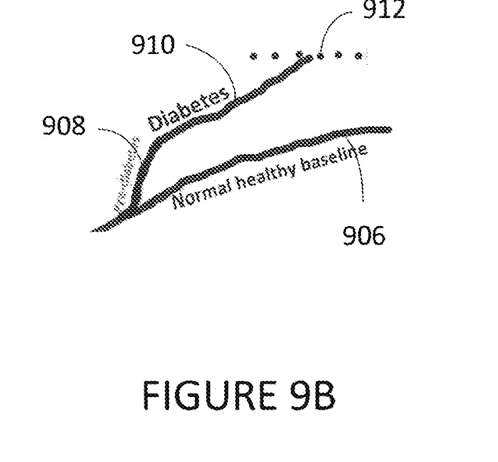
FIG. 9B illustrates a graph utilized for comparing current FFI values in accordance with embodiments herein.

FIGS. 9A and 9B illustrate a graph utilized for comparing current FFI values to normal healthy baseline values that are age-matched and referenced to one or more of prior FFI values during a non-disease state of the patient and one or more of age-normed, gender-normed, or ethnicity-normed baseline, pre-disease, and disease baseline thresholds in accordance with embodiments herein. For example, for normal healthy patient's BG (postprandial <139 mg/Dl, fasting 99-75 mg/dL) average blood glucose between the values but vary individually even for patients that are the same and healthy. As a result, diabetes BG (postprandial >200 mg/dL, fasting >126 mg/dL) diabetes average BG is higher, accelerating the accumulation of FFL. Consequently, as illustrated in the graph 9A, when looking a F/R at 434 nm 902, the F/R tends to increase as individuals age 904, and then average out. As a result a self-reference detection can be provided as illustrated in FIG. 9B to provide a normal healthy baseline 906, pre-diabetes range 908, and a diabetes range 910. To this end, a threshold of complication 912 can also be determined using the methodology. Therefore, depending on whether a patient has a high, medium, or low FFI accumulation, diabetes can be diagnosed accordingly utilizing the methodology provided.

Examples of the present subject matter include:

Example 1 is a method, comprising: under control of one or more processors configured with executable instructions: discriminating an autofluorescence (AF) response of a lens tissue of an eye due to a current level of 1 is missing parent: 1 is missing parent: 2-(2-furoyl)-1 is missing parent: 4(1 is missing parent: 5)-furanyl-1H-imidazole (FFI) in the lens tissue by: interrogating a lens tissue of an eye along a visual axis of the eye by activating an illuminator for a select time to produce interrogating irradiation having a peak wavelength of 425 nm to 460 nm, the illuminator comprising at least one light source and a focal lens positioned with respect to the light source; and obtaining at least one image of the autofluorescence response of the lens tissue from a detector, the detector including a digital camera unit; and analyzing the at least one image to determine a total autofluorescence index of the lens tissue; and determining a current level of FFI in the lens tissue based, at least in part, on the total autofluorescence index.

In Example 2, the subject matter of Example 1 includes wherein the at least one light source includes one or more of a laser diode or a light-emitting diode (LED).

In Example 3, the subject matter of Examples 1-2 includes wherein interrogating further comprises activating the illuminator to produce interrogating radiation having a peak wavelength of 434 nm.

In Example 4, the subject matter of Examples 1-3 includes obtaining the at least one image during or immediately subsequent to the select time.

In Example 5, the subject matter of Example 4 includes wherein the select time is from 2 seconds to 30 seconds.

In Example 6, the subject matter of Examples 4-5 includes wherein the one or more processors are further configured to sequentially repeat the interrogating and obtaining to obtain 2 to 30 images.

In Example 7, the subject matter of Examples 1-6 includes transmitting the at least one image to a remote electronic device via a wireless connection over a network.

In Example 8, the subject matter of Examples 1-7 includes wherein the at least one light source further comprises an array of at least three light sources and interrogating includes pulsing each of the at least three light sources on and off at unique intervals with respect to the remaining ones of the at least three sources.

In Example 9, the subject matter of Examples 1-8 includes wherein the at least one image comprises a plurality of candidate images, and further comprising: analyzing each candidate image of the plurality of candidate images to determine a symmetry value and a definition value of a pupil spot of a pupil; determining at least one confirmed image from the plurality of candidate images based on the symmetry value and the definition value; discerning a median location of a peak value of the at least one confirmed image; and determining the total autofluorescence index based, at least in part, on calculating an average of an area of the median location of the peak value of the at least one confirmed image.

In Example 10, the subject matter of Example 9 includes wherein the median location of the peak value comprises at least an N by N area of pixels.

In Example 11, the subject matter of Example 10 includes wherein the at least and N by N area comprises at least a 5 pixel by 5 pixel area.

In Example 12, the subject matter of Examples 10-11 includes wherein determining the total autofluorescence index includes calculating a normalized total autofluorescence value based on a total autofluorescence value of the at least one confirmed image normalized by the area of the median location.

In Example 13, the subject matter of Example 12 includes wherein determining the total autofluorescence index further comprises normalizing the normalized total autofluorescence value with a calibration value.

In Example 14, the subject matter of Example 13 includes wherein the calibration value comprises a total calibration autofluorescence index.

In Example 15, the subject matter of Example 14 includes wherein determining the total calibration autofluorescence index comprises determining a total calibration autofluorescence value based on at least one calibration image normalized by an area of a calibration median location to determine the total calibration autofluorescence value.

Example 16 is a computer program product comprising a non-transitory computer readable storage medium comprising computer executable code to: discriminate an autofluorescence (AF) response of a lens tissue of an eye due to a current level of 2-(2-furoyl)-4(5)-furanyl-1H-imidazole (FFI) in the lens tissue by: interrogating a lens tissue of an eye along a visual axis of the eye by activating an illuminator for a select time to produce interrogating irradiation having a peak wavelength of 425 nm to 460 nm, the illuminator comprising at least one light source and a focal lens positioned with respect to the light source; and obtaining at least one image of the autofluorescence response of the lens tissue from a detector, the detector including a digital camera unit; and analyze the at least one image to determine a total autofluorescence index of the lens tissue; and determine a current level of FFI in the lens tissue based, at least in part, on the total autofluorescence index.

In Example 17, the subject matter of Example 16 includes computer executable code to, as part of the interrogating, activating the illuminator to produce interrogating radiation having a peak wavelength of 434 nm.

In Example 18, the subject matter of Examples 1-17 includes computer executable code to, as part of the obtaining, obtaining the at least one image during or immediately subsequent to the select time.

In Example 19, the subject matter of Example 18 includes wherein the select time is from 2 seconds to 30 seconds.

In Example 20, the subject matter of Examples 18-19 includes computer executable code to sequentially repeat the interrogating and obtaining to obtain 2 to 30 images.

In Example 21, the subject matter of Examples 16-20 includes computer executable code to transmit the at least one image to a remote electronic device via a wireless connection over a network.

In Example 22, the subject matter of Examples 16-21 includes wherein the at least one image comprises a plurality of candidate images, and includes computer executable code to: analyze each candidate image of the plurality of candidate images to determine a symmetry value and a definition value of a pupil spot of a pupil; determine at least one confirmed image from the plurality of candidate images based on the symmetry value and the definition value; discern a median location of a peak value of the at least one confirmed image; and determine the total autofluorescence index based, at least in part, on calculating an average of an area of the median location of the peak value of the at least one confirmed image.

In Example 23, the subject matter of Example 22 includes wherein the median location of the peak value comprises at least an N by N area of pixels.

In Example 24, the subject matter of Example 23 includes wherein the at least and N by N area comprises at least a 5 pixel by 5 pixel area.

In Example 25, the subject matter of Examples 23-24 includes computer executable code to, as part of determining the total autofluorescence index, calculate a normalized total autofluorescence value based on a total autofluorescence value of the at least one confirmed image normalized by the area of the median location.

In Example 26, the subject matter of Example 25 includes computer executable code to, as part of determining the total autofluorescence index, normalize the normalized total autofluorescence value with a calibration value.

In Example 27, the subject matter of Example 26 includes wherein the calibration value comprises a total calibration autofluorescence index.

In Example 28, the subject matter of Example 27 includes computer executable code to determine a total calibration autofluorescence value based on at least one calibration image normalized by an area of a calibration median location.

Example 29 is at least one machine-readable medium including instructions that, when executed by processing circuitry, cause the processing circuitry to perform operations to implement of any of Examples 1-28.

Example 30 is an apparatus comprising means to implement of any of Examples 1-28.

Example 31 is a system to implement of any of Examples 1-28.

Example 32 is a method to implement of any of Examples 1-28.

CLOSING STATEMENTS

In accordance with at least one embodiment herein, to the extent that mobile devices are discussed herein, it should be understood that they can represent a very wide range of devices, applicable to a very wide range of settings. Thus, by way of illustrative and non-restrictive examples, such devices and/or settings can include mobile telephones, tablet computers, and other portable computers such as portable laptop computers.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified.

The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

Although illustrative example embodiments have been described herein with reference to the accompanying figures, it is to be understood that this description is not limiting, and that various other changes and modifications may be affected therein by one skilled in the art without departing from the scope or spirit of the disclosure.

The modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming.

The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, in the following claims, the phrases "at least A or B", "A and/or B", and "one or more of A and B" (where "A" and "B" represent claim elements), are used to encompass i) A, ii) B and/or iii) both A and B.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method, comprising:
under control of one or more processors configured with executable instructions:
discriminating an autofluorescence (AF) response of a lens tissue of an eye based on a current level of 2-(2-furoyl)-4(5)-furanyl-1H-imidazole (FFI) in the lens tissue by:
interrogating the lens tissue of the eye along a visual axis of the eye with an illuminator to produce interrogating irradiation having a peak wavelength of 425 nm to 460 nm, the illuminator comprising at least one light source and a focal lens positioned with respect to the light source; and
obtaining at least one image of the autofluorescence response of the lens tissue from a detector, the detector including a digital camera unit; and
determining a total autofluorescence index of the lens tissue based on the at least one image; and
determining a current level of FFI in the lens tissue based, at least in part, on the total autofluorescence index.

2. The method of claim 1, wherein interrogating further comprises activating the illuminator to produce interrogating radiation having a peak wavelength of 434 nm.

3. The method of claim 1, wherein the one or more processors are further configured to sequentially repeat the interrogating and obtaining to obtain 2 to 30 images.

4. The method of claim 1, further comprising communicating the at least one image to a remote electronic device via a wireless connection over a network.

5. The method of claim 1, wherein the at least one image comprises a plurality of candidate images, and the method further comprising:
analyzing each candidate image of the plurality of candidate images to determine a symmetry value and a definition value of a pupil spot of a pupil;
determining at least one confirmed image from the plurality of candidate images based on the symmetry value and the definition value;
discerning a median location of a peak value of the at least one confirmed image; and
determining the total autofluorescence index based, at least in part, on calculating an average of an area of the median location of the peak value of the at least one confirmed image.

6. The method of claim 5, wherein the median location of the peak value comprises at least an N by N area of pixels.

7. The method of claim 5, wherein determining the total autofluorescence index includes calculating a normalized total autofluorescence value based on a total autofluorescence value of the at least one confirmed image normalized by the area of the median location.

8. The method of claim 7, wherein determining the total autofluorescence index further comprises normalizing the normalized total autofluorescence value with a calibration value.

9. The method of claim 8, wherein the calibration value comprises a total calibration autofluorescence index.

10. The method of claim 9, wherein determining the total calibration autofluorescence index comprises determining a total calibration autofluorescence value based on at least one calibration image normalized by an area of a calibration median location to determine the total calibration autofluorescence value.

11. A system comprising:
an illuminator including at least one light source and a focal lens positioned to receive light from the light source, the illuminator configured to produce interrogating irradiation having a peak wavelength of 425 nm to 460 nm for interrogating a lens tissue of an eye along a visual axis of the eye;
a detector including a digital camera unit configured to obtain at least one image of the autofluorescence response of the lens tissue;
a processor;
a data storage device having executable instructions accessible by the processor;
wherein, responsive to execution of the instructions, the processor:
determines a total autofluorescence index of the lens tissue based on the at least one image; and
determines a current level of FFI in the lens tissue based, at least in part, on the total autofluorescence index.

12. The system of claim 11, wherein the at least one light source further comprises an array of at least three light sources and interrogating includes pulsing each of the at least three light sources on and off at unique intervals.

13. The system of claim 11, wherein the at least one light source is a light emitting diode or a laser diode.

14. The system of claim 11, wherein the at least one image comprises a plurality of candidate images, and the processor is further configured to:
analyze each candidate image of the plurality of candidate images to determine a symmetry value and a definition value of a pupil spot of a pupil;
determine at least one confirmed image from the plurality of candidate images based on the symmetry value and the definition value;
discern a median location of a peak value of the at least one confirmed image; and determine the total autofluorescence index based, at least in part, on calculating an average of an area of the median location of the peak value of the at least one confirmed image.

15. The system of claim 14, wherein the median location of the peak value comprises at least an N by N area of pixels.

16. A computer program product comprising a non-transitory computer readable storage medium comprising computer executable code to:
discriminate an autofluorescence (AF) response of a lens tissue of an eye due to a current level of 2-(2-furoyl)-4(5)-furanyl-1H-imidazole (FFI) in the lens tissue by:
interrogating a lens tissue of the eye along a visual axis of the eye by activating an illuminator for a select time to produce interrogating irradiation having a peak wavelength of 425 nm to 460 nm, the illuminator comprising at least one light source and a focal lens positioned with respect to the light source; and
obtaining at least one image of the autofluorescence response of the lens tissue from a detector, the detector including a digital camera unit;
analyze the at least one image to determine a total autofluorescence index of the lens tissue; and
determine a current level of FFI in the lens tissue based, at least in part, on the total autofluorescence index.

17. The computer program product of claim 16, further comprising computer executable code to sequentially repeat the interrogating and obtaining to obtain 2 to 30 images.

18. The computer program product of claim 16, further comprising computer executable code to communicate the at least one image to a remote electronic device via a wireless connection over a network.

19. The computer program product of claim 16, wherein the at least one image comprises a plurality of candidate images, and the computer program product further comprising computer executable code to:
analyze each candidate image of the plurality of candidate images to determine a symmetry value and a definition value of a pupil spot of a pupil;
determine at least one confirmed image from the plurality of candidate images based on the symmetry value and the definition value;
discern a median location of a peak value of the at least one confirmed image; and
determine the total autofluorescence index based, at least in part, on calculating an average of an area of the median location of the peak value of the at least one confirmed image.

20. The computer program product of claim 19, further comprising computer executable code to, as part of determining the total autofluorescence index, calculate a normalized total autofluorescence value based on a total autofluorescence value of the at least one confirmed image normalized by the area of the median location.

* * * * *